United States Patent [19]

Ogawa

[11] Patent Number: 4,975,424
[45] Date of Patent: Dec. 4, 1990

[54] METHOD FOR STABILIZING A THIOPHOSPHORIC ACID ESTER

[75] Inventor: Masao Ogawa, Toyonaka, Japan

[73] Assignee: Sumitomo Chemical Company, Limited, Osaka, Japan

[21] Appl. No.: 344,408

[22] Filed: Apr. 28, 1989

Related U.S. Application Data

[63] Continuation-in-part of Ser. No. 258,761, Oct. 17, 1988, abandoned.

[30] Foreign Application Priority Data

Mar. 11, 1988 [JP] Japan ................................. 63-58599

[51] Int. Cl.$^5$ ........................ A01N 57/10; C07F 9/00
[52] U.S. Cl. ........................................ 514/109; 558/7
[58] Field of Search ........................... 558/7; 514/109

[56] References Cited

U.S. PATENT DOCUMENTS

| | | | |
|---|---|---|---|
| 3,760,041 | 9/1973 | Lorenz et al. | 558/7 |
| 4,443,439 | 4/1984 | Ishikawa et al. | 558/7 |
| 4,473,562 | 9/1984 | King | 558/7 |

FOREIGN PATENT DOCUMENTS

| | | |
|---|---|---|
| 2052379 | 4/1972 | Fed. Rep. of Germany . |
| 2163543 | 7/1973 | France . |
| 52-33627 | 3/1977 | Japan . |
| 61-130203 | 6/1986 | Japan . |
| 1121110 | 7/1968 | United Kingdom . |

OTHER PUBLICATIONS

Zimm et al., Fiziol. Akt. Veshchestva, 1987, 19, 14–19, Chemical Abs. vol. 108, 1988, Abs. 89478f.
Kitagaki et al., Japan Kokai 75 40752, Apr. 14, 1975, Chemical Abstracts vol. 83, 1975, Abstract 73534a.

*Primary Examiner*—Mukund J. Shah
*Assistant Examiner*—E. C. Ward
*Attorney, Agent, or Firm*—Stevens, Davis, Miller & Mosher

[57] ABSTRACT

The present invention relates to a method for stabilizing a thiophosphoric acid ester of the formula (I),

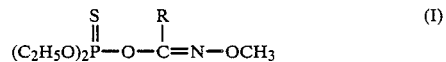

wherein R is a methyl or ethyl group, by adding at least one compound selected from the group consisting of polyols, polyalkylene glycols and their esters and ethers.

According to the present invention, there is provided a highly active and stable soil pest controlling agent and agricultural composition.

8 Claims, No Drawings

METHOD FOR STABILIZING A THIOPHOSPHORIC ACID ESTER

This is a continuation-in-part application of application Ser. No. 258,761, filed Oct. 17, 1988, abandoned.

The present invention relates to a method for stabilizing a thiophosphoric acid ester of the formula (I),

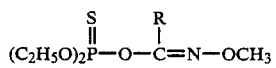
(I)

wherein R is a methyl or ethyl group, and stabilized agricultural compositions containing the same as an active ingredient.

The compounds having the formula (I) (hereinafter referred to as the present compound(s)) has an excellent efficacy against the so-called soil pests living in soil and greatly damaging crops.

The present compound is produced, for example, by the process described below: O,O-diethyl thiophosphoric acid chloride having the formula (II),

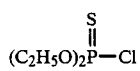
(II)

is treated with N-methoxyamide having the formula (III),

(III)

wherein R has the same meaning described above, in a solvent in the presence of a base.

The physical properties of the present compounds are shown in Table 1.

TABLE 1

| Compound No. | Structure | Physical properties |
|---|---|---|
| (1) | $(C_2H_5O)_2P(\text{S})-O-C(CH_3)=N-OCH_3$ | $n_D^{20.6}$ 1.4638 |
| (2) | $(C_2H_5O)_2P(\text{S})-O-C(C_2H_5)=N-OCH_3$ | $n_D^{23.2}$ 1.4602 |

The present compound exhibits excellent efficacy against various soil pests, for example, pests of Diabrotica genus such as western corn rootworm (*Diabrotica virgifera* Le Conte), northern corn rootworm (*Diabrotica longicornis* Say), southern corn rootworm (*Diabrotica undecimpunctata* howardi Barber), etc.; pests of Anomala genus such as cupreous chafer (*Anomala cuprea* Hope), soybean beetle (*Anomala rufocuprea* Motschulsky), cherry chafer (*Anomala daimiana* Harlod), striated chafer (*Anomala testaceips* Motschulsky), etc.; pests of Popillia genus such as Japanese beetle (*Popillia japonica* Newman), etc.; pests of Aulacophora genus such as cucurbit leaf beetle (*Aulacophora femoralis* Motschulsky), etc.; pests of Phyllotreta genus such as stripped cabbage flea beetle (*Phyllotreta vittata* Fabricius), etc.; pests of Melanotus genus such as sweet potato wireworm (*Melanotus caudex* Lewis), etc.; pests of Agriotes genus such as barley wireworm (*Agriotes fuscicollis* Miwa), etc.; pests of Delia genus such as onion maggot (*Delia antiqua* Meigen), turnip maggot (*Delia floralis* Fallen), seed-corn maggot (*Delia platura* Meigen), etc.; pests of Gryllotalpa genus such as African mole cricket (*Gryllotalpa africana* Palisot de Beauvois), etc.; pests of Lissorhoptrus genus such as rice water weevil (*Lissorhoptrus oryzophilus* Kuschel), etc.; pests of Pratylenchus genus such as Cobb root-lesion nematode (*Pratylenchus penetrans* Cobb), walnut root-lesion nematode (*Pratylenchus vulnus* Allen et Jensen), coffee root-lesion nematode (*Pratylenchus coffeae* Zimmermann), etc.; pests of Heterodera genus such as soybean cyst nematode (*Heterodera glycines* Ichinohe), etc.; pests of Meloidogyne genus such as northern root-knot nematode (*Meloidogyne hapla* Chitwood), cotton root-knot nematode (*Meloidogyne incognita* var. acrita Chitwood), Javanese root-knot nematode (*Meloidogyne javanica* Treub), peanut root-knot nematode (*Meloidogyne arenaria* Neal), etc.; pests of Aphelenchoides genus such as rice white-tip nematode (*Aphelenchoides besseyi* Christie) and the like.

When the present compound is used as an active ingredient for soil pest controlling agents, it is usually formulated before use into oil sprays, emulsifiable concentrates, wettable powders, granules, dusts, aerosols, etc. by mixing with solid carriers, liquid carriers or gaseous carriers, and if necessary, adding surface active agents and/or other auxiliaries for formulation.

It is suitable that these preparations contain the present compound as an active ingredient in an amount of from 0.1 to 99.9% by weight, preferably from 1 to 80% by weight.

However, the present compound sometimes decomposes depending upon the conditions of storage or formulation. The present inventor, therefore, has made an extensive study to establish a method for stabilizing the thiophosphoric acid ester having the formula (I) and obtain stabilized agricultural compositions containing said ester as an active ingredient. As a result, he has confirmed that this object can be attained by using as a stabilizing agent one or more compounds selected from the group consisting of polyols, polyalkylene glycols and their esters and ethers.

Thus, according to the present invention, there are provided a method for stabilizing said ester which method comprises adding to the present compound one or more of the foregoing stabilizing agents and stabilized agricultural compositions obtained by incorporating one or more of the foregoing stabilizing agents in the solid preparations which comprises the present compound as an active ingredient.

As examples of the polyols and polyalkylene glycols used in the stabilization method of the present invention, there are mentioned glycerin, polyglycerin, ethylene glycol (molecular weight: 62), polyethylene glycol having an average molecular weight of not less than 62, propylene glycol (molecular weight 76), polypropylene glycol having an average molecular weight of not less than 76, polybutylene glycol, polyoxyethylene/oxypropylene glycol, polyoxyethylene/oxybutylene glycol, polyoxyethylene/oxypropylene/oxybutylene glycol, etc. In addition, as examples of the polyol esters or ethers and polyalkylene glycol esters or ethers, there are mentioned polyoxyethylene alkyl ester, polyoxyethylene alkyl ether, polyoxyethylene alkylphenol ether, polyoxyethylene sorbitan alkyl ether, their derivatives (e.g. polyoxyethylene alkylphenol ether sodium sulfate, polyoxyethylene sorbitan alkyl ether ammonium sulfate), adducts of sulfuric acid ester series anionic surface active agents with polyoxyalkylene, adducts of sulfonic acid series anionic surface active agents with polyoxyalkylene, etc. However, the polyols, polyalkylene glycols and their esters or ethers which are useful in the stabilization method are not of course limited to those described above. Of these compounds, those which are liquid at room temperature and have a low viscosity are favorable for the purpose of the present invention. Also, propylene glycol, polypropylene glycol, ethylene glycol, polyethylene glycol, glycerin, polyoxyethylene/oxypropylene glycol and polyoxyethylene sorbitan alkyl ether are preferred in various respects.

The stabilization method of the present invention is usually realized by adding from 10 to 300 parts by weight of at least one foregoing stabilizing agent such as polyols, polyalkylene glycols, etc. to 100 parts by weight of the present compound.

The agricultural composition of the present invention contains from 0.1 to 40 parts by weight of the present compound as an active ingredient, from 0.1 to 30 parts by weight, preferably from 1 to 20 parts by weight of the foregoing polyols, polyalkylene glycols, etc. as a stabilizing agent and a solid carrier as the rest. However, various surface active agents and auxiliaries for formulation (e.g. machine oils, liquid paraffin, animal or vegetable oils) may be used together if necessary.

The solid carrier includes for example fine powders or granules of clays (e.g. kaolin clay, diatomite, synthetic hydrated silicon dioxide, bentonite, montmorillonite, terra alba), talcs, other inorganic minerals (e.g. attapulgite clay, sericite, quartz, sulfur, activated carbon, calcium carbonate, hydrated silica, pumice, zeolite), chemical fertilizers (e.g. ammonium sulfate, ammonium phosphate, ammonium nitrate, urea, ammonium chloride), etc. Of these carriers, oil-absorbing granular mineral carriers such as attapulgite clay, diatomite, bentonite, montmorillonite, pumice, zeolite, etc. are so easy to make formulations that they fit the economical production of impregnation-type granules.

Next, formulation examples are shown below: In the examples, parts are by weight.

FORMULATION EXAMPLE 1 GRANULE

Three parts of the present compound (2) are admixed with 6 parts of each of propylene glycol, dipropylene glycol, polypropylene glycol (average molecular weight: 2000), polypropylene glycol (average molecular weight: 4000), glycerin, polyoxyethylene sorbitan monolaurate (number of added moles: 20), polyethylene glycol (average molecular weight: 300) and polyoxyethylene/oxypropylene glycol (average molecular weight: 2500, the ethylene oxide content in all the molecules: 20 wt.%). Thereafter, 91 parts of granular bentonite (a carrier produced by Hojun Mining Co., Ltd.; 14 to 42 mesh) are admixed with each of the resulting mixtures. Then each mixture thus obtained was impregnated into the carrier, whereby granules containing 3% of the active ingredient are obtained.

FORMULATION EXAMPLE 2 GRANULE

Three parts of the present compound (2) are admixed with each of 3 parts and 9 parts of polypropylene glycol (average molecular weight: 2000). Thereafter, the granular bentonite of Formulation example 6 is admixed therewith so as to make the whole 100 parts. Then, each mixture thus obtained was impregnated into the carrier, whereby granules containing 3% of the active ingredient are obtained.

FORMULATION EXAMPLE 3 GRANULE

Three parts of the present compound (2) are admixed with 6 parts of each of polypropylene glycol (average molecular weight: 2000) and polyethylene glycol (average molecular weight: 300). Thereafter, 91 parts of Aplus ® (a carrier produced by Isolite Kogyo Co., Ltd.; granulated and calcined quartz; 20 to 40 mesh) is admixed with each mixture. Then, each of the resulting mixtures was impregnated into the carrier, whereby granules containing 3% of the active ingredient are obtained.

FORMULATION EXAMPLE 4 GRANULE

Three parts of the present compound (2) is admixed with 3 parts of polyethylene glycol (average molecular weight: 300). Thereafter, 94 parts of Ishikawa Lite Pesticide No. 2 ® (a carrier produced by Ishikawa Lite Kogyo Co., Ltd.; pumice) are admixed with the mixture to impregnate the resulting mixture into the carrier, whereby a granule containing 3% of the active ingredient is obtained.

FORMULATION EXAMPLE 5 GRANULE

To 7.5 parts of the present compound (2) are added 10 parts of polyethylene glycol (average molecular weight: 300). Thereafter, 82.5 parts of montmorillonite clay [a carrier produced by Lowe's Co., (Oran Mo.); 24 to 48 mesh] are admixed with the resulting mixture. Then, each mixture thus obtained was impregnated into the carrier, whereby a granule containing 7.5% of the active ingredient is obtained.

FORMULATION EXAMPLE 6 GRANULE

To 7.5 parts of the present compound (2) are added 8 parts of each of propylene glycol, polypropylene glycol (average molecular weight: 2000) and polyethylene glycol (average molecular weight: 300). Thereafter, 84.5 parts of the granular bentonite of Formulation example 6 are admixed with each mixture. Then, each of the resulting mixture was impregnated into the carrier, whereby granules containing 7.5% of the active ingredient are obtained.

FORMULATION EXAMPLE 7 GRANULE

To 3 parts of the present compound (1) are added 6 parts of polypropylene glycol (average molecular weight: 2000). Thereafter, 91 parts of Aplus ® (a carrier described above) are admixed with the mixture. Then the resulting mixture was impregnated into the carrier, whereby granules containing 3% of the active ingredient are obtained.

FORMULATION EXAMPLE 8 DUST

To a mixture of 1 part of the present compound (2), 3 parts of white carbon and 94 parts of kaolin clay are added 2 parts of each of polyethylene glycol (average molecular weight: 300) and polypropylene glycol (average molecular weight: 2000). Every mixture is is uniformly mixed on a mixer to obtain a dust containing 1% of the active ingredient.

FORMULATION EXAMPLE 9 WETTABLE POWDER

To a mixture of 10 parts of the present compound (1) or (2), 2 parts of Sorpo ® 2495 G (an emulsifier produced by Toho Chemical Industries Co., Ltd.), 2 parts of San X ® P-201 (a dispersing agent produced by Sanyo-Kokusaku Pulp Co.. Ltd.), 20 parts of white carbon and 56 parts of diatomite is added 10 parts of each of polyethylene glycol (average molecular weight: 300) and polypropylene glycol (average molecular weight: 2000). Every mixture is uniformly mixed on a mixer to obtain a wettable powder containing 10% of the active ingredient.

COMPARATIVE EXAMPLE 1

Three parts of the present compound (2) are admixed with 97 parts of the granular bentonite of Formulation example 6 to impregnate the present compound into the carrier, whereby a granule containing 3% of the active ingredient is obtained.

COMPARATIVE EXAMPLE 2

Three parts of the present compound (2) are admixed with 97 parts of Aplus ® of Formulation example 8 to impregnate the present compound into the carrier, whereby a granule containing 3% of the active ingredient is obtained.

COMPARATIVE EXAMPLE 3

Three parts of the present compound (2) are admixed with 97 parts of Ishikawa Lite Pesticide No. 2 ® of Formulation example 9 to impregnate the present compound into the carrier, whereby a granule containing 3% of the active ingredient is obtained.

COMPARATIVE EXAMPLE 4

To 7.5 parts of the present compound (2) are added 92.5 parts of the montmorillonite clay of Formulation example 10 to impregnate the present compound into the carrier, whereby a granule containing 7.5% of the active ingredient is obtained.

COMPARATIVE EXAMPLE 5

To 7.5 parts of the present compound (2) are added 92.5 parts of the granular bentonite of Formulation example 6 to impregnate the present compound into the carrier, whereby a granule containing 7.5% of the active ingredient is obtained.

COMPARATIVE EXAMPLE 6

To 3 parts of the present compound (1) are added 97 parts of Aplus ® of Formulation example 7 to impregnate the present compound into the carrier, whereby a granule containing 3% of the active ingredient is obtained.

TEST EXAMPLE 1

The mixtures comprising 50 parts of the present compound (2) and 50 parts of each of polyethylene glycol (average molecular weight: 300) and polypropylene glycol (average molecular weight: 2000) were put into glass bottle and then subjected to the heat-storage test. The mixture comprising 50 parts of the present compound and no stabilizing agent and the mixtures comprising 50 parts of the present compound and 50 parts of each of toluene, heptane and acetone were also subjected to the same test as a control. The test gave the present decomposition of the active ingredient.

Tables 2 and 3 show the results.

TABLE 2

| Stabilizing agent | Percent decomposition (%) (after storage at 40° C. for 7 days) |
| --- | --- |
| Polypropylene glycol (average molecular weight: 2000) | 0 |
| Polyethylene glycol (average molecular weight: 300) | 7.1 |
| None | 29.3 |

TABLE 3

|  | Percent decomposition (%) (after storage at 40° C. for 6 days) |
| --- | --- |
| Toluene | 20.6 |
| Heptane | 15.6 |
| Acetone | 23.5 |

TEST EXAMPLE 2

The heat-storage test was carried out on the compositions obtained in Formulation examples 1 and 2 and Comparative example 1 to measure the percent decomposition of the active ingredient.

Table 4 shows the results.

TABLE 4

| Stabilizing agent | Dosage rate (%) | Percent decomposition (%) (after storage at 40° C. for 30 days) |
| --- | --- | --- |
| Propylene glycol | 6 | 1.2 |
| Dipropylene glycol | 6 | 4.5 |
| Polypropylene glycol (average molecular weight: 2000) | 3 | 8.9 |
|  | 6 | 2.7 |
|  | 9 | 7.1 |
| Polypropylene glycol (average molecular weight: 4000) | 6 | 1.5 |
| Glycerin | 6 | 3.2 |
| Polyoxyethlene sorbitan monolaurate (20 moles of oxyethylene added) | 6 | 0.6 |
| Polyethylene glycol (average molecular weight: 300) | 6 | 2.7 |
| Polyoxyethylene/oxypropylene glycol (average molecular weight: 2500, ethylene oxide content in all the molecules: 20 wt. %) | 6 | 4.7 |
| None | — | 97.9 |

TEST EXAMPLE 3

The heat-storage test was carried out on the compositions obtained in Formulation example 3 and Comparative example 2 to measure the percent decomposition of the active ingredient.

Table 5 shows the results.

TABLE 5

| Stabilizing agent | Percent decomposition (%) (after storage at 40° C. for 30 days) |
| --- | --- |
| Polypropylene glycol (average molecular weight: 2000) | 3.3 |
| Polyethylene glycol (average molecular weight: 300) | 0 |

TABLE 5-continued

| Stabilizing agent | Percent decomposition (%) (after storage at 40° C. for 30 days) |
|---|---|
| None | 27.6 |

TEST EXAMPLE 4

The heat-storage test was carried out on the compositions obtained in Formulation example 4 and Comparative example 3 to measure the percent decomposition of the active ingredient.

Table 6 shows the results.

TABLE 6

| Stabilizing agent | Percent decomposition (%) (after storage at 40° C. for 30 days) |
|---|---|
| Polyethylene glycol (average molecular weight: 300) | 3.0 |
| None | 95.2 |

TEST EXAMPLE 5

The heat-storage test was carried out on the compositions obtained in Formulation example 5 and Comparative example 4 to measure the precent decomposition of the active ingredient.

Table 7 shows the results

TABLE 7

| Stabilizing agent | Percent decomposition (%) (after storage at 40° C. for 30 days) |
|---|---|
| Polyethylene glycol (average molecular weight: 300) | 8.9 |
| None | 99.2 |

The heat-storage test was carried out on the compositions obtained in Formulation example 6 and Comparative example 5 to measure the percent decomposition of the active ingredient.

Table 8 shows the results.

TABLE 8

| Stabilizing agent | Percent decomposition (%) (after storage at 40° C. for 30 days) |
|---|---|
| Polypropylene glycol (average molecular weight: 2000) | 9.3 |
| Polyethylene glycol (average molecular weight: 300) | 6.0 |
| Propylene glycol | 4.3 |
| None | 94.2 |

TEST EXAMPLE 7

The heat-storage test was carried out on the compositions obtained in Formulation example 7 and Comparative example 6 to measure the percent decomposition of the active ingredient.

Table 9 shows the results.

TABLE 9

| Stabilizing agent | Percent decomposition (%) (after storage at 40° C. for 14 days) |
|---|---|
| Polypropylene glycol (average molecular weight: 2000) | 0.7 |
| None | 71.0 |

Next, the usefulness of the present compound as an active ingredient for soil pest controlling agents is demonstrated with reference to the following reference example.

REFERENCE EXAMPLE

Each of 40 parts of the present compound (1) and (2) was dissolved in 50 parts of xylene, and 10 parts of an emulsifier, Sorpol SM-200 (a registered trade mark of Toho Chemical Industries Co., Ltd.; a mixture of polyoxyethylene alkylaryl ether, etc. and dodecylbenzenesulfonic acid), are added thereto. The resulting mixture is well stirred and mixed to obtain an emulsifiable concentrate having an active ingredient concentration of 40%.

Five milliliters of aqueous diluted solution of each of the emulsifiable concentrates obtained above was mixed with 50 g of soil to give a soil samples having an active ingredient content in the soil of 0.5 or 0.25 ppm.

Each of these soil samples was filled in a polyethylene cup of 5.6 cm in diameter and 5.8 cm in height. In each cup, two corn grains having roots 2 to 3 cm long were planted and 10 third-instar larvae of southern corn rootworm (*Diabrotica undecimpunctata howardi* BARBER) were released. After two days, the number of the dead and alive larvae were counted for mortality (%). This test was repeated three times. Table 10 shows the results.

TABLE 10

| Test compound | Mortality (%) | |
|---|---|---|
| | 0.5 ppm | 0.25 ppm |
| Present compound (1) | 100 | 100 |
| Present compound (2) | 100 | 100 |

What is claimed is:

1. A method for stabilizing a thiophosphoric acid ester which comprises adding at least one compound selected from the group consisting of glycerin, polyglycerin, ethylene glycol (molecular weight: 62), polyethylene glycol having an average molecular weight of not less than 62, propylene glycol (molecular weight: 76), polypropylene glycol having an average molecular weight of not less than 76, polybutylene glycol, polyoxyethylene/oxypropylene glycol, polyoxyethylene/oxybutylene glycol, polyoxyethylene/oxypropylene/oxybutylene glycol, polyoxyethylene alkyl ester, polyoxyethylene alkyl ether, polyoxyethylene alkylphenol ether, polyoxyethylene sorbitan alkyl ether, their derivatives, adducts of sulfuric acid ester series anionic surface active agents with polyoxyalkylene and adducts of sulfonic acid series anionic surface active agents with polyoxyalkylene to a thiophosphoric acid ester of the formula (I),

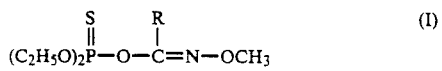

wherein R is methyl or ethyl.

2. A method for stabilizing a thiophosphoric acid ester which comprises adding at least one compound selected from the group consisting of propylene glycol, polypropylene glycol, ethylene glycol, polyethylene glycol, glycerin, polyoxyethylene/oxypropylene glycol and polyoxyethylene sorbitan alkyl ether to a thiophosphoric acid ester of the formula (I),

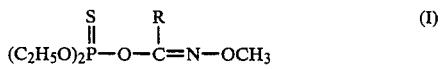

wherein R is methyl or ethyl.

3. A stabilized agricultural composition which is obtained by incorporating at least one compound selected from the group consisting of glycerin, polyglycerin, ethylene glycol (molecular weight: 62), polyethylene glycol having an average molecular weight of not less than 62, propylene glycol (molecular weight: 76), polypropylene glycol having an average molecular weight of not less than 76, polybutylene glycol, polyoxyethylene/oxypropylene glycol, polyoxyethylene/oxybutylene glycol, polyoxyethylene/oxypropylene/oxybutylene glycol, polyoxyethylene alkyl ester, polyoxyethylene alkyl ether, polyoxyethylene alkylphenol ether, polyoxyethylene sorbitan alkyl ether, their derivatives, adducts of sulfuric acid ester series anionic surface active agents with polyoxyalkylene and adducts of sulfonic acid series anionic surface active agents with polyoxyalkylene into a solid preparation comprising a thiophosphoric acid ester of the formula (I),

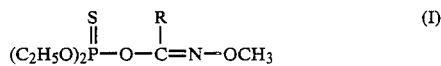

wherein R is methyl or ethyl.

4. A composition according to claim 3 further comprising at least one oil-absorbing granular mineral carrier.

5. A composition according to claim 3, wherein the amount of the thiophosphoric acid ester is 0.1 to 40 parts by weight and the amount of the compound is 0.1 to 30 parts by weight.

6. A stabilized agricultural composition which is obtained by incorporating at least one compound selected from the group consisting of propylene glycol, polypropylene glycol, ethylene glycol, polyethylene glycol, glycerin, polyoxyethylene/oxypropylene glycol and polyoxyethylene sorbitan alkyl ether into a solid preparation comprising a thiophosphoric acid ester of the formula (I), $$(C_2H_5O)_2\overset{\overset{S}{\|}}{P}-O-\overset{\overset{R}{|}}{C}=N-OCH_3 \quad (I)$$

wherein R is methyl or ethyl.

7. A composition according to claim 6, further comprising at least one oil-absorbing granular mineral carrier.

8. A composition according to claim 6, wherein the amount of the thiophosphoric acid ester is 0.1 to 40 parts by weight and the amount of the compound is 0.1 to 30 parts by weight.

* * * * *